(12) United States Patent
Lamberti

(10) Patent No.: US 6,193,989 B1
(45) Date of Patent: Feb. 27, 2001

(54) LONG ACTING INJECTABLE PARASITICIDAL COMPOSITION AND THE PROCESS FOR ITS PREPARATION

(75) Inventor: Jorge Carlos Lamberti, Buenos Aires (AR)

(73) Assignee: Biogenesis S.A., Buenos Aires (AR)

( * ) Notice: Subject to any disclaimer, the term of this patent is extended or adjusted under 35 U.S.C. 154(b) by 0 days.

(21) Appl. No.: 09/163,567

(22) Filed: Sep. 30, 1998

Related U.S. Application Data

(63) Continuation-in-part of application No. 09/035,870, filed on Mar. 6, 1998, now Pat. No. 6,054,140.

(30) Foreign Application Priority Data

Mar. 21, 1997 (AR) ................................................. 970101168

(51) Int. Cl.[7] .................................................... A01N 25/02
(52) U.S. Cl. .............................. 424/405; 514/30; 514/937
(58) Field of Search ..................................... 424/405–406; 514/30, 937

(56) References Cited

FOREIGN PATENT DOCUMENTS

413538 * 8/1991 (EP).
9505812 * 3/1995 (WO).

* cited by examiner

*Primary Examiner*—Neil S. Levy
(74) *Attorney, Agent, or Firm*—Birch, Stewart, Kolasch & Birch, LLP.

(57) ABSTRACT

The present invention is drawn to a long acting injectable parasiticide composition comprising ivermectin in a 1% (w/w) concentration, benzilic alcohol, polyvinyl pyrrolidone, N-methyl-2-pyrrolidone in proportion of 40–65% (v/w) of the total formulation. The present invention is further drawn to methods of making using and using thereof.

8 Claims, No Drawings

LONG ACTING INJECTABLE PARASITICIDAL COMPOSITION AND THE PROCESS FOR ITS PREPARATION

This application is a continuation-in-part Application, claiming priority under 35 U.S.C. §120 to U.S. application Ser. No.: 09/035,870, filed Mar. 6, 1998, now U.S. Pat. No. 6,054,140.

An object of this invention is a new long acting injectable parasiticide composition and the process for its preparation.

Ivermectin is a semisynthetic derivative formed by a mixture of two components, 22,23-dihydroavermectin $B_{1a}$ and 22,23-dihydroavermectin $B_{1b}$. Initial avermectin $B_1$ is a macrocyclic lactone obtained from *Streptomyces avermitilis* culture fermentation broth and the selective hydrogenation of the existing double bonds in the C22–C23 position of avermectin $B_1$ macrolid structures leads to the synthesis of ivermectin as described in literature.

Ivermectin, a macrocyclic lactone, whose developed formula is:

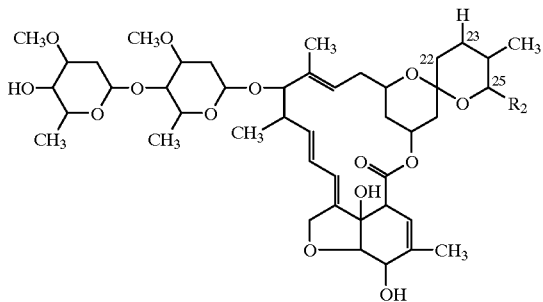

where R2 is isopropyl (20%) or sec-butyl (80%), is a broad spectrum antiparasitic not only against internal parasites, but also against external parasites and even endoparasitic stages of several arthropods. It is active against nemathod genera which affect pets and cattle such as Trichostrongyloidea, Strongyloidea, Metastrongyloidea, Rhabditoidea, Ascaridoidea, Oxyuroidea, Spiruroidea, Filaroidea and Trichurioidea superfamilies. Its high solubility, high body penetration and long term average life, account for the broad use of ivermectin as antihelminthic.

The normal way to administer antiparasiticides to large animals is orally. Patents EP 473223, EP 537000, EP 537998 and U.S. Pat. No. 4,440,740 describe solid formulations of ivermectin.

Highly efficient injectable formulations have also been described and their handy application triggered the appearance of a series of preparations, such as the ones described in the following patents which are related with liquid administration forms: EP 146414, EP 413538, EP 535734, EP 538750 and U.S. Pat No. 4,389,397.

More specifically, patent EP 146414, protects certain non watery liquid formulations which contain ivermectin and more precisely, those which contain ivermectin 1% in a vehicle formed by a mixture of 40% formal glycerol—60% propylene glycol.

The object of the present invention is a novel injectable, long acting parasiticidal composition which contains ivermectin and which presents comparatively superior pharmakinetic properties over known formulations.

Said novel, long acting, injectable parasiticidal composition presents acceptable levels of residue for the consumption of beef by humans, in conditions of total safety. The European Union has settled maximum residue quantities for ivermectin in bovines at 100 ug/kg in liver and 40 ug/kg in fat.

Likewise, the object of the present invention is a process for the preparation of said novel injectable, long acting parasiticidal composition.

Therefore, the object of the present invention is an injectable, long acting parasiticidal composition which comprises enough ivermectin to achieve a final concentration of about 1% (w/w), benzilic alcohol, polyvinylpyrrolidone, N-methyl-2-pyrrolidone in a 40–65% proportion (v/w) of the total formulation and glycerin until completing final 100% weight.

Besides these components, the formulation may contain stabilizers/antioxidants such as thiodipropionic acid, acetyl cysteine, cysteine, sodium metabisulfite, EDTA, sodium EDTA, sodium citrate, N-propyl gallate, butyl-hydroxy-toluene or a mixture of more than one of these products in a 0.01 to 2% w/w proportion. Optionally, the formulation may also contain a coloring such as betacarotene, in a 0.005–0.05 w/w proportion.

Another object of the present invention is the procedure to prepare an injectable, long acting parasiticidal composition which involves mixing enough ivermectin to obtain a final concentration of about 1% (w/w) with benzilic alcohol and polyvinylpyrrolidone followed by the addition of the mixture to N-methyl-2-pyrrolidone, the latter in a 40–65% proportion (v/w) of the total of the formulation. Afterwards, the antioxidant or mixture of antioxidants dissolved in water if necessary, are added. The mixture is shaken until totally dissolved and glycerin is added until reaching 100% final weight.

Polyvinylpyrrolidone that has been used in the composition of the invention is Kollidon K 17 PF with a K 16–18 value and a relative viscosity of the solution in distilled water at 5% from 1.250–1.370. Kollidon K 17 PF is preferably used in a proportion between 7–11% (w/w) of the total of the mixture.

Benzilic alcohol is incorporated to the mixture in an appropriate proportion to achieve a final concentration between 1.5 and 2% (w/w).

The object of the following examples is to illustrate the invention for a better understanding without trying to introduce limitations.

EXAMPLE 1

Preparation of the Composition 1.000 g of Ivermectin, 8.977 g Kollidon K 17 PF and 1.795 benzilic alcohol in 53.860 ml of N-Metyl-2-Pyrrolidone (Pharmasolve) are dissolved in a stainless steel container. Later, 0.03 g of N-propyl gallate are added. The mixture is shaken until it is totally dissolved. It is taken to 100.000 g with glycerin. The resulting solution is prefiltered and finally filtered in a Nylon 66 or Teflon terminal filter of 0.45 microns pore diameter.

EXAMPLE 2

Pharmakinetic Behavior of an Ivermectin 1% w/w in N-Metyl-2-Pyrrolidone and Polyvinyl Pyrrolidone Composition Prepared Pursuant to Example 1

6 castrated, male, healthy Argentine Holstein animals were separated. Their weight was between 150–200 kg. The animals were wormed with a benzoimidazolic product 20 days before the start of the test.

The composition described in Example 1 was administered to the animals subcutaneously in a 1 ml per each 50 kg rate. Blood samples were taken in heparinized syringes previously to administration and afterwards following this schedule: 0.5, 1, 2, 3, 4, 5, 6, 7, 8, 10, 12, 15, 20, 25 and 30 days. Plasma was separated by centrifugation and stored until its testing. The trial was performed with high pressure liquid chromatography with ultraviolet detection. Thus, the samples were treated by liquid solid extraction in C18 cartridges. After this process, they were injected in the chromatographer. Ivermectin extraction percentage was 80%. Quantification level of the method was 0.5 ng/ml. Repetitivity had a variation of less than 2% for a 5 ng/ml concentration. Pharmakinetic analysis was performed through a lineal regression program called strip (Brown and Manno, 1978). Pharmakinetic parameters were obtained by classical methods.

Ivermectin concentrations versus time are shown in Table 1. Plasmatic profile of ivermectin can be appreciated in FIG. 1 in which concentration versus time has been represented. The area under curve (AUC) which, in this case, is 300, indicates which percentage of the dosage effectively reaches plasma and contributes to pharmacological action. Pharmakinetic parameters are shown in Table II.

Obtained results show higher plasmatic peaks and plasmatic concentrations that last longer than classical ivermectin preparations such as those prepared in propylenglycol-glycerol that were previously mentioned. In this case, an average maximum concentration (Cmax) of 30 ng/ml (Table 1, day 3) and an AUC of 300 (FIG. 1) were found. However, the most distinctive characteristic with respect to said known formulations is found in the midlife of elimination (T1/2 B in Table II) which in this experience rendered an almost 9 days average, as opposed to the known formulations which have elimination midlives of about 5–6 days. Likewise, concentrations on day 30 in this experiment render a 2.81 ng/ml average while they are 1 ng/ml for classical mentioned compositions.

TABLE I

Ivermectin plasmatic concentrations after the administration of a 1% w/w formulation in N-metyl-2-pyrrolidone and polyvinyl pyrrolidone to 6 young bovines-1 ml every 50 kg.

| HPA | 1 | 2 | 3 | 4 | 5 | 6 | X ± sd |
|---|---|---|---|---|---|---|---|
| 0.5 | 1.21 | 4.70 | 5.60 | 6.60 | 5.38 | 3.72 | 4.70 ± 2.07 |
| 1 | 3.20 | 22.19 | 20.72 | 9.54 | 15.68 | 31.24 | 17.09 ± 9.91 |
| 2 | 8.47 | 23.70 | 25.40 | 18.93 | 23.37 | 21.60 | 20.25 ± 6.17 |
| 3 | 27.15 | 30.56 | 32.56 | 27.88 | 31.54 | 34.81 | 30.68 ± 2.87 |
| 4 | 15.75 | 21.41 | 29.87 | 16.54 | 32.33 | 20.01 | 20.82 ± 5.04 |
| 5 | 18.40 |  | 25.12 | 20.17 | 24.92 | 19.05 | 21.53 ± 3.25 |
| 6 | 22.12 | 21.17 | 22.63 | 15.51 | 19.75 | 20.01 | 20.20 ± 2.56 |
| 7 | 18.50 | 16.64 | 20.40 | 12.04 | 14.99 | 18.94 | 16.92 ± 3.04 |
| 8 | 15.87 | 12.91 | 19.35 | 10.85 | 12.38 | 11.32 | 13.71 ± 3.26 |
| 10 | 12.17 | 11.92 | 15.21 |  | 11.40 | 10.70 | 12.28 ± 1.73 |
| 12 | 10.93 | 8.66 | 11.57 | 7.62 | 9.34 | 9.81 | 9.66 ± 1.45 |
| 15 | 8.36 | 7.14 | 9.82 | 6.37 | 7.72 | 6.28 | 7.62 ± 1.34 |
| 20 | 6.72 | 4.17 | 7.47 | 2.35 | 5.58 | 3.70 | 5.0 ± 1.94 |
| 25 | 5.60 | 3.42 | 5.94 | 1.24 | 4.31 | 3.44 | 4.0 ± 1.71 |
| 30 | 3.21 | 2.08 | 4.66 |  | 2.40 | 1.89 | 2.81 ± 1.18 |

TABLE II

Pharmakinetic parameters for an Ivermectine 1% w/w preparation in N-metyl-2-pyrrolidone and polyvinyl pyrrolidone in six young bovines after a subcutaneous administration

| Param. | 1 | 2 | 3 | 4 | 5 | 6 | X ± SD |
|---|---|---|---|---|---|---|---|
| A | −64.25 | 19.75 | 96.59 | −5.43 | 101.86 | 7.94 |  |
| α | 0.15 | 0.22 | 0.4 | 0.21 | 0.59 | 0.29 | 0.31 ± 0.16 |
| B | 83.57 | 17.1 | 19.07 | 34.3 | 24.55 | 26.93 | 34.25 ± 24.92 |
| β | 0.11 | 0.07 | 0.047 | 0.13 | 0.077 | 0.093 | 0.09 ± 0.03 |
| Kabs | 0.83 | 2 | 0.68 | 1.05 | 0.89 | 0.64 | 1.02 ± 0.5 |
| T 1/2α | 110.88 | 75.6 | 41.58 | 79.2 | 28.19 | 57.35 | 65.47 ± 29.59 |
| T 1/2β | 6.3 | 9.9 | 14.7 | 5.3 | 9 | 7.5 | 8.8 ± 3.3 |
| T 1/2 abs | 0.84 | 0.35 | 1.02 | 0.66 | 0.78 | 1.08 | 0.79 ± 0.26 |

EXAMPLE 3

Determination of Ivermectin Residues after the Administration of a 1% w/w Ivermectin Composition in N-metyl-2-pyrrolidone and Polyvinyl Pyrrolidone Prepared in Accordance with Example 1

21 calves between 100–150 kg were separated. The composition identified in Example 1 was subcutaneously administered to them, 1 ml every 50 kg. As from day 0 (administration) 3 animals were put to death weekly from the third to the ninth week.

Plasma, liver, fat, muscle, injected area muscle and kidney samples were taken.

5 g. samples were homogenized in Ultra-Turrax for 2 minutes with 15 ml acetonitrile. The homogenate was centrifugated 5 minutes at 300 rpm. 15 ml of supernatant was transferred to jars and dissolved with water until a 70% watery solution was obtained. 50 µl of triethylamine were added.

C8 bond-Elut cartridges were activated with acetonitrile and acetonitrile: water (30:70). Total sample was passed through cartridge C8. The cartridge was eluted with 5 ml acetonitrile and the eluate was evaporated under nitrogen. The residue was resuspended in 1 ml methanol. Proportional 500 µl were transferred to a silaned tube and evaporated. 100 µl of the deriving agent (1-methyl -imidazole-acetic anhydride-dimethylformamide) (2:6:9) were added and the tube was sent to the oven at 95° C. for an hour. After the cooling, 1 ml chloroform was added, it was subjected to vortical motion and transferred to Sep-Pack cartridges. The cartridge was eluted with 9 ml of chloroform, evaporated and resuspended in 500 µl of methanol and injected in the high pressure system of liquid chromatography with fluorometric detection (HPLC). Chromatographic conditions were: Mobile stage: acetonitrile: water (97:3); Flow: 1 ml/min.; Excitation: 364 mm.

Results are expressed in ppb as averages of the observed concentrations in every trio of animals, in Table III.

According to residual limits settled by the European Union, experimental animals used in this study showed an average of concentrations in target tissue within the range that is considered acceptable for consumption, as from the 41 days following post-administration.

TABLE III

Ivermectin concentrations in several tissues and plasma between the third and ninth weeks post administration of the Composition prepared according to Example 1, in samples of animals treated subcutaneously with 1 ml every 50 kg of weight

| days | inj. zone. | sartorius | lever | kidney | plasma | fat |
|---|---|---|---|---|---|---|
| 21 | 1467.5 | 16.24 | 72.9 | 27.45 | 7.65 | 67.62 |
| 28 | 53.36 | 19.32 | 25.97 | 13.55 | 3.49 | 45.77 |
| 35 | 15.73 | 8.24 | 21.88 | 7.08 | 1.9 | 40.93 |
| 43 | 10.69 | 7.74 | 18.71 | 5.01 | 0.32 | 14.38 |
| 49 | 7.43 | 4.93 | 12.93 | 4 | n.d | 8.4 |
| 55 | 2.01 | 0.72 | 3.21 | n.d. | n.d. | 1.6 |
| 62 | n.d. | n.d. | n.d. | n.d. | n.d. | n.d. |

EXAMPLE 4

Effectiveness Trial of the New Ivermectine 1% Injectable Formulation Obtained in Accordance with Example 1, Against Common Bovine Tick, *Boophilus microplus* (Can.), in Stabled Heifers with Experimental Infestation A 30 Hereford heifer lot, 9–12 months old weaning was weighed, tagged and stored in a single, large, semi shaded pen for its taming and feeding staying in said pen for a month and a half. During the last 3 weeks they received experimental infestation of 20,000 *Boophilus microplus* larvae a week (approximately 6,666 larvae in 3 weekly infestations) by spreading and back lumbar extension.

The 20 animals with more parasites were selected on day 0 of the treatment and were sent alternatively to two groups, Treated Group (TG) and Control Group (CG), determining TG at random. The animals were lodged in single, roofed boxes, tied with halters and rope to a ring so as to avoid dressing up. Each box had a floor properly fitted to collect detached teleogines. Treated Group animals were given a subcutaneous 1 ml/50 kg live weight doses of the composition of the invention.

The collection, counting and weighing of detached teleogines was daily performed. They were placed in Petri plates and in heaters at 28° C. and 80% REH (relative environmental humidity). Day 10, after discarding dead specimens, survival percentage was recorded. Day 18 following the start of the hatching, the total weight of the hatching of the aliquot of each plate was recorded and, taking 1 g of the total in a test tube, the eclosion percentage at day 14 could be determined. All the data collected through this methodology was applied to formulas that make it possible to define the efficiency of the product. Applied formulas are based in the Drummond originals modified by Weidhass et al (1989) at the CSIRO (Australia) and by Rodriguez et al (1990) at the "Centro de Ingeniería Genética y Biotecnologia" (CIGB) in La Habana (Cuba). Said formulas are stated as follows:

a) Teleogine (Tg) Knock-down Effect
1. Teleogine Reduction Percentage $$\% TR = 100 \times \left(1 - \frac{\text{Total amount of } Tg \text{ of } TG}{\text{Total amount of } Tg \text{ of } CG}\right)$$

TRC (Teleogine Reduction Coefficient)=100×(1-%TR)
b) Effect over Detached Teleogines
2. Percentage of Repletion Reduction $$\% RR = 100 \times \left(1 - \frac{(\bar{x}) \, Tg \text{ Weight of } TG}{(\bar{x}) \, Tg \text{ Weight of } CG}\right)$$

where:

$$\text{Weight } (\bar{x}) \text{ of } Tg = \frac{\text{Total Weight of } Tg \text{ of Incubated Aliquot}}{\text{Total Weight of } Tg \text{ Survivors}}$$

RRC (Repletion Reduction Coefficient)=100×(1-%RR)
3. Survival Reduction Percentage (Tg Mortality)

$$\% SR = 1 - \left(\frac{\frac{\text{Total Live } Tg \text{ of } TG \text{ Aliquots}}{\text{Total } Tg \text{ of } TG \text{ Aliquots}}}{\frac{\text{Total Live } Tg \text{ of } CG \text{ Aliquots}}{\text{Total } Tg \text{ of } CG \text{ Aliquots}}}\right)$$

SRC (Survival Reduction Coefficient)=100×(1-%SR)
4. Hatching Reduction Percentage $$\% HR = 100 \times \left(1 - \frac{(\bar{x}) \text{ Weight of } Tg \text{ hatching of } TG}{(\bar{x}) \, Tg \text{ Hatching of } CG}\right)$$

where:

Hatching $Tg$ ($\bar{x}$) Weight =

$$\frac{\text{Total Hatching Weight of Inoculated } Tg}{\text{Total Amount of Surviving } Tg}$$

HRC (Hatching Reduction Coefficient)=100×(1-%HR)
5. Fertility Reduction Percentage (Eclosion)

$$\% FR = 100 \times \left(1 - \frac{\text{Total } TG \, (\bar{x}) \text{ Larvae Weight}}{\text{Total } CG \, (\bar{x}) \text{ Larvae Weight}}\right)$$

where:

$$\text{Larvae Weight } (\bar{x}) = \frac{\text{Total Larvae Weight}}{\text{Incubated Egg Grams}}$$

FRC (Fertility Reduction Coefficient)=100×(1-%FR)
6. Efficiency Percentage
%EP=100×(1-TRC×HRC×FRC)

Analyzed parameters and both Groups compared (Treaty and Control) between days 0 and 23 inclusive, rendered the following results:
Teleogine Reduction Percentage (knock-down): 92.92%
Repletion Reduction Percentage: 23.60%
Survival Reduction Percentage: 27.64%
Hatching Reduction Percentage: 59.29%
Fertility Reduction Percentage (eclosion): 51.97%
Efficiency Percentage (23 days post treatment): 98.62%

The trial showed the new invention formulation presents a high knock-down rate with a high Teleogine mortality rate. During the first 24 post treatment hours, TG only added 181 specimens while CG (control) added 270 (67.4% reduction), indicating high mortality over the animal, which did not become detached. The following 72 hours, 65 detached teleogines were collected (average 21.6 per day) and 781 from the CG (daily average of 260), probably as a result of immature elements that could not complete their cycle because of treatment. As from day 5 post treatment, and during the rest of the trial, no TG teleogines were collected while CG continued releasing this adult stage until day 23 inclusive with a total 3516 (152.8 average per day).

EXAMPLE 5

Effectiveness Trial of the New Injectable 1% Ivermectine Formulation Obtained in Accordance with Example 1 in a Single Subcutaneous Doses against Ovine Mange (*Psorotes ovis*)

65 Corriedale and cross breed ovines between 14 and 87 kg. were stored, all presenting natural active mange infection spreaded in extensive injuries covering approximately 30% of the body.

Day 0 three Groups were formed: Group I (green tag) received two doses of the composition obtained in accordance with Example 1, with a 7 day interval (200 mcg/kg) equivalent to 0.5 ml/25 kg of live weight; Group II (red tag) received a single doses (300 mcg/kg) equivalent to 1 ml/30 kg. live weight while Group III was inoculated with 30% overdoses to control innocuousness.

Every ovine was weighted and infestation recorded in a separate form specially designed for these trials and, after assigning them to the Groups, were treated as necessary (the allocation of the Group and its treatment was done at random), placing them afterwards in separate pens during the whole of the trial.

Groups I and II were checked at day 15 and 35 after treatment of the second or single doses according to the treatment, while Group III (innocuity) was examined for 5 days to monitor adverse symptoms.

Day 15, all ovines (Groups I and II) were free of live acarus, and remained like that on day 35; cure of injures became apparent on day 15 and was totally achieved on day 35. No adverse reactions were registered in any ovine of the three Groups, including Group III, those who received the overdoses.

These results made it possible to determine comparative advantages of the long lasting formulation of the present invention. Prior art formulations had showed efficiency against *Psoroptes ovis*, through the application of 200 mcg/kg in two doses with an interval between them of 7 to 9 days. The change in the pharmacokinetic profile of this new injectable formulation, with special long lasting features, of 1% avermectine in N-methyl-2-pirrolidone and polyvinyl pirrolidone, has allowed for the elimination of mange in ovines (*Psorotes ovis*) with a single subcutaneous injection of 300 mcg/kg.

The possibility of applying a single doses for ovine mange presents clear advantages, such as lower labor costs and, with regards to the product, the saving of time when sanitary assisting flocks.

EXAMPLE 6

Efectiveness Trial of the New Ivermectin 1% Injectable Formulation Obtained in Accordance with Example 1, in a Single Subcutaneous Doses, against *Melophagus ovinus* (Linnaeus, 1758) in Sheep

*Melophagus ovinus* is included in the Pupipara group (Hippoboscidae family, Latreille 1796) (Soulsby, 1993). True fly without wings, also called "false tick" is adapted to parasitary life. It is ovine exclusive, feeding itself on blood during its adult stage. It feeds every 12 hours, damaging leather for the manufacture industry. In 1985, losses were estimated in 41 million dollars per year in the US.

With reference to treatment, pour on of 2% cyalothrin, 6% cypermethrin and 1% decamethrin formulations were evaluated, not being able to verify 100% control with any of said products 10 days after treatment.

Basically a melophaguicide product, applied during or immediately after clipping, should show a 95% efficacy or more at day 14 (control of adult specimens), of 100% after 28 days (control of new emerging generation from the pupas), keep that control until day 42, and should not affect the quality of the fleece or the health of the animal. Immersion products, dorsal pouring, spraying and sprinkling (Merck Veterinary Manual, 1986) would not comply with all these premises. Classical, 1% single doses, injectable, classical endoparasiticides, are not able to keep minimum levels of drug plasmatic concentration after 4 weeks to ensure the control of the new generation or the reinfestation. With a conventional 1%, injectable ivermectin formulation, (in propylene-glycerol), the need to use 2 injections with a 21 day interval has been ratified to achieve cleaning (day 49) and protection against reinfestation (42 days) of 100%.

A work that allowed to evaluate the efficacy of the new injectable 1% ivermectin long lasting composition in a single doses of 300 mcg/kg, for the control of *Melophagus ovinus* is described hereinafter. The use of a single doses, applied during clipping, constitutes a positive contribution for the simultaneous control of *Melophagus ovinus* and ovine mange (*Psorotes ovis*), as described in Example 5 above.

40 lambs and young Merino muttons not clipped were selected. Their infestation was recorded and were assigned at random to 2 Groups (Treated G.I and Control G.II). Both groups were clipped and lodged in separate pickets. G.I was treated with the composition of the invention (Example 1) subcutaneously at a 1 ml/30 kg live weight rate. After treatment observations were carried out at day 14, 28 and 40.

Results of the adult melophagus recount in Group I (treated) and Group II (control), is summarized in the following Chart:

|      | Day-3 |     |     | +14 |      |     | +28 |     |     | +40 |     |     |
|------|-------|-----|-----|-----|------|-----|-----|-----|-----|-----|-----|-----|
|      | (1)   | (2) | (3) | (1) | (2)  | (3) | (1) | (2) | (3) | (1) | (2) | (3) |
| G.I  | 240   | 12  | 20  | 1   | 0.05 | 1   | 0   | 0   | 0   | 0   | 0   | 0   |
| G.II | 192   | 9.6 | 19  | 38  | 1.9  | 9   | 6   | 0.3 | 2   | 4   | 0.2 | 4   |

(1) Total parasites.
(2) Arithmetic mean of the total amount of adult flies in 20 ovines of the Group;
(3) Amount of ovines with parasites.

Parasite level was reduced substantially on day +14 only due to clipping, which in G.II (control) achieved the 80% in the total number of adult flies, while in 11/20 ovines, no specimens were found (55%). The opportunity of treatment immediately after clipping was stated in the first place as most of the infestation was eliminated together with the fleece—both in adults and in pupas—and, secondly, that the new microclimate created in the clipped animal would be less advantageous for the life of the surviving false tick. However, in this untreated Group parasitation was kept—even though at inferior levels—during the 40 days of the trial and allowed for the comparative evaluation of the efficiency of the injected product.

In the G.I (treated), at day +14 the release of the false tick achieved the 99.6% (p<0.01) and the only sample was found in a 76 kg. mutton which was under dosified with only 2 ml. The control was total (100%) at 28 days and remained stable at 40 days after treatment, stating that the plasmatic level of ivermectin in the long lasting composition of the invention, efficiently acted over the new generation of flies, as they hatched from the L3 of the pupas.

EXAMPLE 7

Effectiveness Trial of the New Ivermectin 1% Injectable Formulation, Obtained in Accordance with Example 1, against *Dermatobia hominis* (Linnaeus, 1781), in Calves with Infestation, in Two Separate Field Trials

*Dermatobia hominis* is a characteristic fly of Latin America, which larvae produce serious damages in cattle.

Death of calves due to abscesses or to suspended sucking, secondary miasis, delay and reduced calf price at the weaning, serious delays in fattening, less milk production, price devaluation of the leathers, are some of the damages caused by this ectoparasite., which is known as "ura" in Argentina and Paraguay.

Two simultaneous field trial were performed with 1–3 month old calves, in two farms ("San Cristóbal" and "San Justo") which geographically far. Three Groups of 10 calves each, with natural infestation, were formed for each trial. In "San Cristóbal" farm the calves were of indic race and in "San Justo" farm they were Brangus and Braford race.

Group A was treated with a conventional ivermectin 1% w/w injectable formulation (propylen-glycol formal) in a subcutaneous dose of 200 μg/kg (1 ml/kg live weight).

Group B was treated with the injectable, long lasting composition of the invention, obtained in accordance with Example 1, that is 1% ivermectin in N-metyl-2-pyrrolidone and polyvinyl pyrrolidone, in a 200 μg/kg dose (1 ml/kg live weight).

Group C was the control non-treated group. It was formed by calves with less quantity of nodules with alive larvae.

Results are shown below:

A) "San Cristóbal" farm (Misiones Province)

1) Total number of nodules in the three Groups (n=10)

|  | Days | | | | | | |
| --- | --- | --- | --- | --- | --- | --- | --- |
|  | 0 | 7 | 14 | 21 | 28 | 35 | 42 |
| G.A. | 218 | 0 | 0 | $0^b$ | 0 | 5 | $8^b$ |
| G.B. | 228 | 0 | 0 | $0^b$ | 0 | 0 | $2^b$ |
| G.C. | 173 | 164 | 286 | $311^{a(*)}$ | (311) | (311) | $(311)^a$ |

[a]values with different letters in the column are significantly different (p < 0.05)
(*)treated on day 21 with the composition of the invention
(311): values of GC at day 21, projected to 28, 35 and 42 days.

2) Efficiency Percentage $$PE = \frac{Nr\ \%\ of\ nodules\ 0\ day - Nr\ \%\ of\ nodules\ n\ day}{Nr\ \%\ of\ de\ nodules\ 0\ day}$$

|  | Days | | | | | |
| --- | --- | --- | --- | --- | --- | --- |
|  | 7 | 14 | 21 | 28 | 35 | 42 |
| G.A. | 100 | 100 | 100 | 100 | 97.7 | 96.3 |
| G.B. | 100 | 100 | 100 | 100 | 100 | 99.1 |

3) Protection Percentage $$PP = \frac{Nr\ \%\ of\ nodules\ of\ GT\ (GA\ or\ GB)}{N°\ \%\ de\ nódulos\ del\ GC}\ Nr\ \%\ of\ nodules\ of\ GC -$$

|  | Days | | | | | |
| --- | --- | --- | --- | --- | --- | --- |
|  | 7 | 14 | 21 | 28 | 35 | 42 |
| G.A. | 98 | 100 | 94.3 | 92.9 | 85.3 | 76.3 |
| G.B. | 100 | 100 | 100 | 100 | 100 | 96.0 |

Note: EP and PP of days 28, 35 and 42 were calculated in GT by comparing the recount on day 21 in the GC (control), when this group was treated due to high reinfestation.

B) "San Justo" farm (Corrientes Province)

1) Total number of nodules in the three Groups (n=10)

|  | Days | | | | | | |
| --- | --- | --- | --- | --- | --- | --- | --- |
|  | 0 | 7 | 14 | 21 | 28 | 35 | 42 |
| G.A. | 156 | 3 | 3 | 8 | $11^b$ | 20 | $37^b$ |
| G.B. | 151 | 0 | 0 | 0 | $0^b$ | 0 | $6^b$ |
| G.C. | 37 | 65 | 120 | 157 | $211^{(*)a}$ | (211) | $(211)^a$ |

[a]values with different letters in the column are significantly different (p < 0.05)
(*)treated on day 21 with the composition of the invention
(211): values of GC at day 28, projected to 35 and 42 days.

2) Efficacy Percentage $$PE = \frac{Nr\ \%\ of\ nodules\ 0\ day - Nr\ \%\ of\ nodules\ n\ day}{Nr\ \%\ of\ de\ nodules\ 0\ day}$$

|  | Days | | | | | |
| --- | --- | --- | --- | --- | --- | --- |
|  | 7 | 14 | 21 | 28 | 35 | 42 |
| G.A. | 98 | 100 | 94.3 | 92.9 | 83.3 | 76.3 |
| G.B. | 100 | 100 | 100 | 100 | 100 | 96.0 |

3) Protection Percentage $$PP = \frac{Nr\ \%\ of\ nodules\ of\ GT\ (GA\ or\ GB)}{N°\ \%\ de\ nódulos\ del\ GC}\ Nr\ \%\ of\ nodules\ of\ GC -$$

|  | Days | | | | | |
| --- | --- | --- | --- | --- | --- | --- |
|  | 7 | 14 | 21 | 28 | 35 | 42 |
| G.A. | 95.4 | 100 | 94.9 | 94.8 | 87.7 | 82.5 |
| G.B. | 100 | 100 | 100 | 100 | 100 | 97.2 |

Note: EP and PP of days 35 and 42 were calculated in comparison with the recount on day 28 in the GC (control), when this group was treated due to high reinfestation.

Among other results, fast death of larvae was registered in G.B (100%), mainly between 12 and 24 hs and totall death before 48h postreatment, with their expulsion (>90%) before day 7; elimination of remaining death larvae in their nodules was completed at day 14. Nodules of G. B compared against G.A (conventional 1% injectable ivermectin) healed in a dry process without infectious material, while G.A nodules, in substantial amount, showed suppuration.

In case of having extended the trials up to days 56 and 63 (the trials were suspended due to reasons beyond the assays), the high protection percentages achieved at day 42 with the composition of the invention, forecasted the achievement of an acceptable control at weeks 8 and 9 postreatment.

Having described and determined the nature of the present invention and the way in which it shall be performed, what is claimed as property and exclusive right is:

1. A method of treating parasites in an animal, comprising:
   administering to said animal by injection an antiparacitically effective amount of a composition, said composition comprising:
   ivermectin in a 1% (w/w) concentration;
   benzyl alcohol in a concentration amount of about 1.5 to 2% (w/w);
   polyvinyl pyrrolidone in a concentration amount of about 7 to 11% (w/w);
   N-methyl-2-pyrrolidone in a concentration amount of about 40 to 65% (v/w); and
   glycerin until reaching 100% final weight.

2. The method of claim 1, wherein said parasite is an external parasite.

3. The method of claim 1, wherein said parasite is an internal parasite.

4. The method of claim 3, wherein said internal parasite is a nematode.

5. The method of claim 3, wherein said internal parasite is a family member selected from the group consisting of Trichostrongyloidea, Strongyloidea, Metastrongyloidea, Rhabditoidea, Ascaridoidea, Oxyuroidea, Spiruoidea, Filaoidea, and Trichurioidea.

6. The method of claim 3, wherein said external parasite is *Boophilus microplus* or *Melophagus ovinus*.

7. The method of claim 2, wherein said external parasite causes the mange.

8. The method of claim 1, wherein said animal is an ovine or a bovine.

* * * * *